United States Patent [19]

Walsdorf et al.

[11] Patent Number: 5,219,889

[45] Date of Patent: Jun. 15, 1993

[54] DIETARY SUPPLEMENTATION WITH POTASSIUM MAGNESIUM CITRATE

[75] Inventors: Neill B. Walsdorf; George Alexandrides, both of San Antonio; Charles Y. C. Pak, Dallas, all of Tex.

[73] Assignees: The University of Texas System, Austin; Mission Pharmacal Company, San Antonio, both of Tex.

[21] Appl. No.: 803,689

[22] Filed: Dec. 3, 1991

Related U.S. Application Data

[60] Continuation of Ser. No. 437,938, Nov. 16, 1989, abandoned, which is a continuation-in-part of Ser. No. 303,536, Jan. 27, 1989, Pat. No. 4,895,980, which is a division of Ser. No. 140,818, Jan. 5, 1988, Pat. No. 4,985,593.

[51] Int. Cl.⁵ ............................................. A61K 31/19
[52] U.S. Cl. .................................................... 514/574
[58] Field of Search ................ 514/474, 574; 562/584; 424/10

[56] References Cited

U.S. PATENT DOCUMENTS

| | | | |
|---|---|---|---|
| 3,086,928 | 4/1963 | Schulz | 424/600 |
| 4,738,856 | 4/1988 | Clark | 424/600 |
| 4,895,980 | 1/1990 | Walsdorf et al. | 514/574 |
| 4,985,593 | 1/1991 | Walsdorf et al. | 562/584 |

FOREIGN PATENT DOCUMENTS 968843 4/1958 Fed. Rep. of Germany.
55-108814 8/1980 Japan.

OTHER PUBLICATIONS

Avery's Drug Treatment, 3rd ed. (1987) pp. 643–648.
Yendt, E. R. et al. 1978. "Prevention of Calcium Stones With Thiazides", Kidney International, vol. 13, pp. 397–409.
Nicar, M. J. et al. 1984. "Use of potassium citrate as potassium supplement during thiazide therapy of calcium nephrolithiasis". The Journal of Urology, vol. 131.
Rudman, D. et al. 1980. "Hypocitraturia in Patients With Gastrointestinal Malabsorption". The New England Journal of Medicine, vol. 303, pp. 657–661.
Pak, C. Y. C. 1987. "Citrate and Renal Calculi". Mineral and Electrolyte Metabolism, vol. 13, pp. 257–266.
Pak, C. Y. C. et al. 1985. "Correction of Hypocitraturia and Prevention of Stone Formation by Combined Thiazide and Potassium Citrate Therapy in Thiazide-Unresponsive Hypercalciuric Nephrolithiasis". The American Journal of Medicine, vol. 79, pp. 284–288.
Barilla, D. E. et al. 1978. "Renal Oxalate Excretion Following Oral Oxalate Loads in Patients with Ileal Disease and with Renal and Absorptive Hypercalciurias". The American Journal of Medicine, vol. 64, pp. 579–585.
Sakhaee, K. et al. 1983. "Contrasting Effects of Potassium Citrate and Sodium Citrate Therapies on Urinary Chemistries and Crystallization of Stone-Forming Salts", Kidney International, vol. 24, pp. 348–352.
Pak, C. Y. C. et al. 1985. "Long-Term Treatment of Calcium Nephrolithiasis With Potassium Citrate". The Journal of Urology. vol. 134, pp. 11–19.
Harvey, J. A. et al. 1985. "Calcium Citrate: Reduced Propensity for the Crystallization of Calcium Oxalate in Urine Resulting From Induced Hypercalciuria of Calcium Supplementation". Journal of Clinical Endocrinology and Metabolism. vol. 61, pp. 1223–1225.
Preminger, G. M., et al., 1989. "Hypomagnesiuric Hypocitraturia: An Apparent New Entity for Calcium Nephrolithiasis". Journal of Lithotripsy and Stone Diesase, vol. 1, pp. 22–25.
Putzar, et al. (1979) Chemical Abstracts, vol. 90, No. 56264q.

Primary Examiner—Frederick E. Waddell
Assistant Examiner—Raymond J. Henley, III
Attorney, Agent, or Firm—Ross, Howison, Clapp & Korn

[57] ABSTRACT

A method for supplementing dietary potassium, magnesium and citrate is disclosed that comprises orally administering an effective amount of potassium magnesium citrate in a single salt. Methods for decreasing urinary calcium and oxalate by the administration of potassium magnesium citrate in a single salt are also disclosed.

3 Claims, 2 Drawing Sheets

5,219,889

DIETARY SUPPLEMENTATION WITH POTASSIUM MAGNESIUM CITRATE

A portion of the development of the present invention was supported by Grant No. P01-DK20543 from the United States Public Health Service and the National Institutes of Health.

CROSS-REFERENCE TO RELATED APPLICATIONS

This application is a continuation of application Ser. No. 437,938, filed Nov. 16, 1989, now abandoned, which is a continuation-in-part of application Ser. No. 07/303,536, filed Jan. 27, 1989, now U.S. Pat. No. 4,895,980 which is a divisional of application Ser. No. 07/140,818, filed Jan. 5, 1988 now U.S. Pat. No. 4,985,593.

TECHNICAL FIELD

This invention relates to dietary supplementation, and more particularly, to a method for supplementing dietary potassium and magnesium through the oral administration of potassium magnesium citrate. Another aspect of the invention relates to a method for increasing urinary pH, potassium, magnesium and citrate through the oral administration of potassium magnesium citrate. Another aspect of the invention relates to a method for decreasing urinary calcium and oxalate through the oral administration of potassium citrate.

BACKGROUND OF INVENTION

The use of magnesium salts for dietary supplementation is well known. Unfortunately, the beneficial effects derived from dietary magnesium supplementation have too often been achieved at the expense of other undesirable side effects such as acute diarrhea. Another disadvantage of the commercially available dietary magnesium supplements has been the relatively large tablet size required to obtain the desired magnesium dosage.

The use of potassium supplements such as potassium chloride for the treatment of patients with hypokalemia is also well known. Here again, however, problems have been encountered with associated side effects such as arrhythmia and diarrhea.

Recently, it has been learned that some of these undesirable side effects can be better controlled by administering potassium in combination with magnesium citrate. Nevertheless, due to the relatively low densities of the commercially available magnesium citrate preparations, the large tablet sizes required to obtain a desirable dosage remain a problem.

In view of the medically recognized need for supplementing dietary potassium and magnesium under certain circumstances, and in view of recently published data demonstrating the improved uptake and bioavailability of these minerals when administered in combination with citrate, a method is therefore needed for supplementing dietary potassium, magnesium and citrate in such manner that undesirably large tablet sizes or numbers of tablets are required in order to attain a desired dosage.

SUMMARY OF THE INVENTION

According to the present invention, a method is disclosed that is believed to significantly and unexpectedly improve the supplementation of dietary potassium and magnesium through the administration of a single composition comprising both potassium and magnesium together with citrate in a single salt.

According to one preferred embodiment of the invention, a method for supplementing dietary potassium and magnesium is disclosed that comprises orally administering tetrapotassium monomagnesium dicitrate to a patient in need of such supplementation.

According to another embodiment of the invention a method for supplementing dietary potassium is disclosed that comprises orally administering tetrapotassium monomagnesium dicitrate to a patent in need of such supplementation.

According to another embodiment of the invention, a method for increasing the urinary citrate excretion of a patient is disclosed that comprises orally administering effective amounts of tetrapotassium monomagnesium dicitrate.

According to another embodiment of the invention, a method for increasing the urinary magnesium excretion of a patient is disclosed that comprises orally administering effective amounts of tetrapotassium monomagnesium dicitrate.

According to another embodiment of the invention, a method for decreasing the urinary calcium of a patent is disclosed that comprises orally administering effective amounts of tetrapotassium monomagnesium dicitrate.

According to another embodiment of the invention, a method for decreasing the urinary oxalate of a patent is disclosed that comprises orally administering effective amounts of tetrapotassium monomagnesium dicitrate.

The present invention is believed to provide dietary potassium, magnesium and citrate in a form that is more efficiently absorbed than prior art compositions, and with fewer or less severe side effects.

Dietary supplements so disclosed herein have a preferred potassium:magnesium:citrate molar ratio, and can be readily compacted into a easily ingestible tablet form. When the subject composition is produced as a pharmaceutical grade, directly compressible material as disclosed herein, only one or two excipients are required, with no preprocessing.

The method of the invention will be better understood upon reading the following description of the preferred embodiments, and by reference to the accompanying examples.

BRIEF DESCRIPTION OF THE DRAWINGS

The preferred composition utilized in practicing the method of the invention and the beneficial results achieved through use of the present invention are further described and explained in relation to the following figures of the drawings wherein.

DESCRIPTION OF THE PREFERRED EMBODIMENT

A new compound, a dual mineral salt, has now been synthesized by reacting stoichiometric quantities of citric acid, a magnesium compound and a potassium compound, preferably as follows:

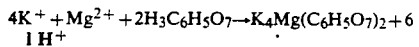
$$4K^+ + Mg^{2+} + 2H_3C_6H_5O_7 \rightarrow K_4Mg(C_6H_5O_7)_2 + 6 H^+$$

Figure 1:
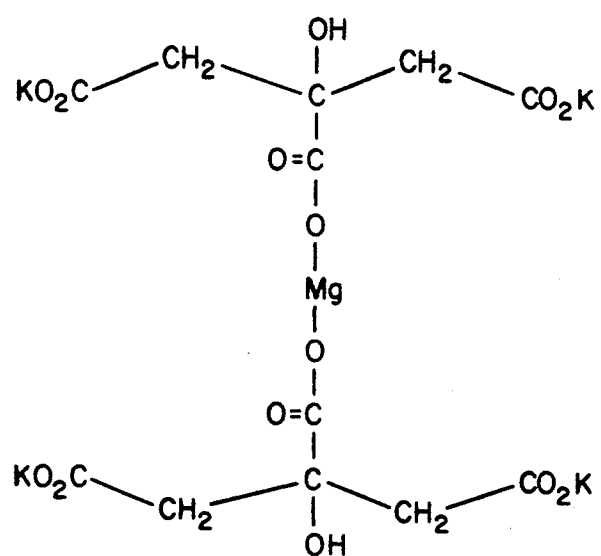
FIG. 1 is a diagrammatic representation of the structural formula believed most likely to correspond to the structure of tetrapotassium monomagnesium dicitrate prepared as disclosed herein and preferred for use in practicing the method of the invention.

Although the structure of the resultant product is not known with certainty, a likely structural formula for the preferred product is shown in FIG. 1.

Depending upon reaction conditions and the relative concentrations of the reactants, the monopotassium form of the composition of the invention can also be produced in a competing reaction as follows:

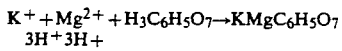
$$K^+ + Mg^{2+} + H_3C_6H_5O_7 \rightarrow KMgC_6H_5O_7 3H^+ 3H+$$

The reaction is preferably initiated by the slow addition of the magnesium compound to a mixture of water and citric acid, followed by the slow introduction of the potassium compound to the reaction mixture.

The magnesium compound is preferably selected from the group consisting of magnesium carbonate, magnesium oxide and magnesium hydroxide. Magnesium oxide is the preferred magnesium compound from a cost standpoint, although the use of magnesium carbonate will provide better control over the temperature of the reaction mixture. The potassium compound is preferably selected from the group consisting of potassium carbonate and potassium bicarbonate, with potassium carbonate being generally preferred because of its lower cost.

The citric acid is mixed with water with uninterrupted agitation, and the magnesium compound and potassium compound are thereafter sequentially mixed with the citric acid to produce a dense, hydrated mixture. This dense hydrated mixture may be characterized as being a thick "slush" comprising potassium ions, magnesium ions and citrate ions in a proportion of about 4:1:2.

During addition of the magnesium compound, the temperature of the mixture is desirably controlled below about 100° C. by controlling the rate of addition. If the temperature of the reaction mixture is permitted to rise above about 120° C., product degradation may occur. A preferred temperature for the reaction mixture during and following addition of the magnesium compound is about 80° C.

The hydrated mixture preferably has a water content between about 10 weight percent and about 20 weight percent. If the water content falls below about 10 weight percent, it is likely that the reaction will be incomplete. Above about 20 weight percent, the mixture retains a paste-like consistency for a longer period of time, which is economically disadvantageous.

This hydrated mixture is thereafter preferably blended in a ribbon mixer to a granular mass consisting of granules and lumps. The mass is then milled and dried to produce a potassium magnesium citrate composition having a maximum particle size of about ⅛ inch (0.3 cm) in diameter and a moisture content ranging between about 0 weight percent and about 5 weight percent. The potassium magnesium citrate composition thus produced has a bulk density (weight per gross volume) preferably ranging from about 1.0 g/cc to about 1.3 g/cc, and most preferably, greater than about 1.1 g/cc. Milling and sizing this bulk material produces a granular pharmaceutical material suitable for tableting.

This bulk potassium magnesium citrate composition is a preferred precursor for the production of potassium magnesium citrate tablets as it represents a densified source of potassium, magnesium and citrate, and is directly compressible. A tableting composition is formed by subjoining and blending it with a lubricant, such as magnesium stearate.

A retarded release tableting composition is formed by subjoining and blending potassium magnesium citrate, a lubricant such as magnesium stearate and a wax material such as carnauba wax. Each of these tableting compositions is then fed through a multiple-station tablet press to form potassium magnesium citrate tablets.

The preferred magnesium potassium citrate tablets thus formed preferably comprise about 27 weight percent potassium, 4 weight percent magnesium, 68 weight percent citrate, and have a potassium:magnesium:citrate molar composition of 4:1:2. Non-wax matrix tablets characteristically have a density of about 1.7 g/cc and wax matrix tablets have a density of about 1.5 g/cc. For aesthetic or other purposes, these tablets may be coated by conventional means with mixtures comprising substances such as sugar, polyvinylpyrrolidone, calcium carbonate and titanium oxide, or the like.

The tetrapotassium monomagnesium dicitrate composition of the invention is a potent delivery system yielding 7.0 meq of potassium (274 mg), 3.5 meq of magnesium (42 mg) and 10.5 meq of citrate (662 mg) in each 10.5 meq tablet of potassium magnesium citrate (978 mg).

The present invention will be better understood by reference to the following examples:

EXAMPLE 1

Citric acid powder (120 g) and water (30 g) were thoroughly mixed in a large beaker. Pure magnesium oxide (12.6 g) was added with rapid stirring. Potassium carbonate powder (86.4 g) was introduced in four approximately equal portions, each portion added after the $CO_2$ evolution had slowed or ceased. Water (10 g) was added to complete the reaction. After drying, the material was sized and found to have a bulk density greater than 1.1 g/cc. Tablet density was determined by an Archimedean method. This dense granular potassium magnesium citrate was subjected to compression tableting and tablets containing 3.5 meq (42 mg) of magnesium, 7.0 meq (274 mg) of potassium and 10.5 meq (662 mg) of citrate, with a size of 0.28 (7.11 mm) inch by 0.62 inches (1.6 cm) were produced, even without the addition of binders.

EXAMPLE 2

The ultradense potassium magnesium citrate tablets of the invention were also produced on a large scale. Citric acid powder (48.03 kg, 250 moles) and water (12 kg) were placed in a Colton 7 cu. ft. ribbon mixer and blended for 2 minutes. The magnesium oxide (5.04 kg, 125 moles) was added in approximately three equal portions, 3 minutes apart with continuous mixing. Potassium carbonate (69.1 kg, 500 moles) was added in approximately three equal portions 5 minutes apart with continuous mixing. Water (4 kg) was added in order to complete the reaction Mixing continued for 2-5 minutes. The resultant granular and lumpy material was passed through a Fitzmill, knives forward, with no screen, trayed and dried at 150° F. (66° C.) for three hours. The dried product was sized and its bulk density was determined to be greater than 1.1 g/cc. The sizing was done using a Fitzmill Model No. 6 with a 3162AA screen.

The dried potassium magnesium citrate composition was subjoined with 1.0 weight percent magnesium stearate. The tableting composition was then tableted in a multiple station tablet press to form potassium magnesium citrate tablets comprising at least about 42 mg of magnesium, 274 mg of potassium and 662 mg of citrate. Multiple station tablet presses such as a Cotton #216-16 station press; a Vector #247-41 station press; or a Manesty Rotopress-37 station press, for example, may be used. The tablets thus obtained may be final products or may be further processed.

Further processing to physically and aesthetically improve these tablets may be accomplished by tablet coating procedures well known to those skilled in relevant pharmaceutical arts. For example, a coating comprising polyvinylpyrrolidone (PVP), sugar, water, calcium carbonate and titanium dioxide was placed on these tablets. This coating procedure was by conventional pharmaceutical pan-coating technology.

EXAMPLE 3

The procedure from Example 2 was followed with the magnesium oxide being replaced by magnesium carbonate. A potassium magnesium citrate having a bulk density of greater than 1.1 g/cc was produced.

EXAMPLE 4

The procedure from Example 2 was followed with the magnesium oxide being replace by magnesium hydroxide. A potassium magnesium citrate having a bulk density of greater than 1.1 g/cc was produced.

EXAMPLE 5

The procedures of Examples 2, 3 and 4 are followed using potassium bicarbonate instead of potassium carbonate. Again potassium magnesium citrate having a bulk density of greater than 1.1 g/cc is produced.

EXAMPLE 6

Magnesium potassium citrate produced by the methods in Examples 2-5 can be used in the preparation of slow release or retarded release tablets by subjoining it with a wax material such as carnauba wax. The dried, sized potassium magnesium citrate made in accordance with the invention was subjoined with 1.0 weight percent magnesium stearate and 13.2 weight percent carnauba wax. After blending the ingredients for 5 minutes, tableting in the Manesty rotopress yielded tablets having a density of 1.6 g/cc or one tablet per 0.7cc. Each such tablet contained 978 mg of magnesium potassium citrate and the USP (Method II) dissolution pattern indicated the following:

| Hours Elapsed | Percentage Dissolved |
|---|---|
| 0.5 | 35.7 |
| 1.0 | 48.4 |
| 2.0 | 68.5 |
| 3.0 | 81.6 |
| 4.0 | 91.5 |
| 5.0 | 94.8 |

| Hours Elapsed | Percentage Dissolved |
|---|---|
| 6.0 | 100.0 |

This dissolution profile should prevent known side effects encountered with other potassium preparations, despite the fact that the wax level is minimal.

By orally administering tableted pharmaceutical compositions as disclosed herein, or in such other dosages as may be deemed effective by persons trained in medicine and licensed to prescribe such supplements, one can easily supplement dietary potassium, magnesium and citrate in a patent needing such supplementation.

It is known that thiazides probably represent the most popular treatment regimen for hypercalciuric nephrolithiasis. They have even been advocated for the management of calcium nephrolithiasis associated with normocalciuria.

However, there are certain problems with thiazide therapy which may limit its utility in nephrolithiasis. First, thiazides may cause hypokalemia and magnesium depletion by provoking renal loss of potassium and magnesium. Particularly common in older subjects, this complication may cause muscle weakness, cramping and serious cardiac arrhythmias.

Second, the induced potassium and magnesium loss may impair renal excretion of citrate, a recognized inhibitor of the crystallization of calcium salts. The resulting reduction in inhibitor activity may cause a relapse in stone formation during thiazide therapy, by opposing the hypocalciuric action of thiazide. Despite numerous reports of the utility of thiazide in the control of hypercalciuric nephrolithiasis, experience with the use of thiazide alone has not been entirely satisfactory, with a relapse rate of 37.5-57.1%.

The above problems may be partly overcome by potassium citrate. It has previously been shown that potassium citrate averts the development of hypokalemia in hypercalciuric patients with nephrolithiasis treated with thiazide, augments citrate excretion and prevents recurrent stone formation in patients who have relapsed on thiazide therapy.

However, potassium citrate therapy does not avert thiazide-induced magnesium depletion. This need theoretically may be met by magnesium citrate. Magnesium citrate has been shown to be more soluble and absorbable than magnesium oxide. Unfortunately, magnesium citrate was also shown to have an equivalent magnesiuric and citraturic effect as magnesium oxide, when magnesium salts were provided in small divided doses.

Another problem with potassium citrate is poor patient compliance due to the small amount of potassium citrate (5 meq) contained in each tablet. Thus a patient maintained an average dose of Urocit-K (50 meq/day) needs to take 10 tablets of this medication per day.

The benefits available to patients through dietary supplementation with tetrapotassium monomagnesium dicitrate as disclosed herein are believed attributable to its unexpected desirable formulation characteristic. Thus, a single tablet of potassium magnesium citrate contains 7 meq potassium, 3.5 meq magnesium and 10.5 meq citrate. In contrast, the currently available formulation of potassium citrate (Urocit-K) of the same size as potassium magnesium citrate has only 5 meq potassium (29% less), 5 meq citrate (52% less) and no magnesium.

Consider a patient taking a typical dose of potassium citrate 50 meq/day. The patient would need to take 10 tablets in order to provide 50 meq potassium and 50 meq citrate. In contrast, the patient would require only 7 tablets of potassium magnesium citrate in order to provide an equivalent amount of potassium (49 meq), more citrate (73.5 meq) as well as magnesium (24.5 meq).

The value of the tetrapotassium monomagnesium dicitrate composition disclosed herein as a dietary supplement is also enhanced by its excellent solubility. Four tablets of potassium magnesium citrate (containing 28 meq K, 14 meq Mg and 42 meq citrate, representing a high single dose) were found to be completely soluble in 300 ml water (without HCl) at 37 degrees C. after 15 min. incubation.

EXAMPLE 7

A study was done to demonstrate the excellent bioavailability of potassium, magnesium and citrate when administered orally in the form of tetrapotassium monomagnesium dicitrate prepared as disclosed herein. The study was performed with three normal subjects. Qualitatively similar findings were observed. The results in one subject are detailed below:

The subject underwent three phases of study. During one phase, the patient took potassium citrate (10 tablets Urocit-K or 50 meq potassium and citrate), at another time magnesium citrate (2.5 tablets containing 25 meq magnesium and citrate), and at a third time potassium magnesium citrate (7 tablets containing 49 meq K, 73.5 meq citrate and 24.5 meq Mg). Urine was collected at frequent intervals for 24 hours after oral ingestion of each salt (at 8 a.m.).

Figure 2:
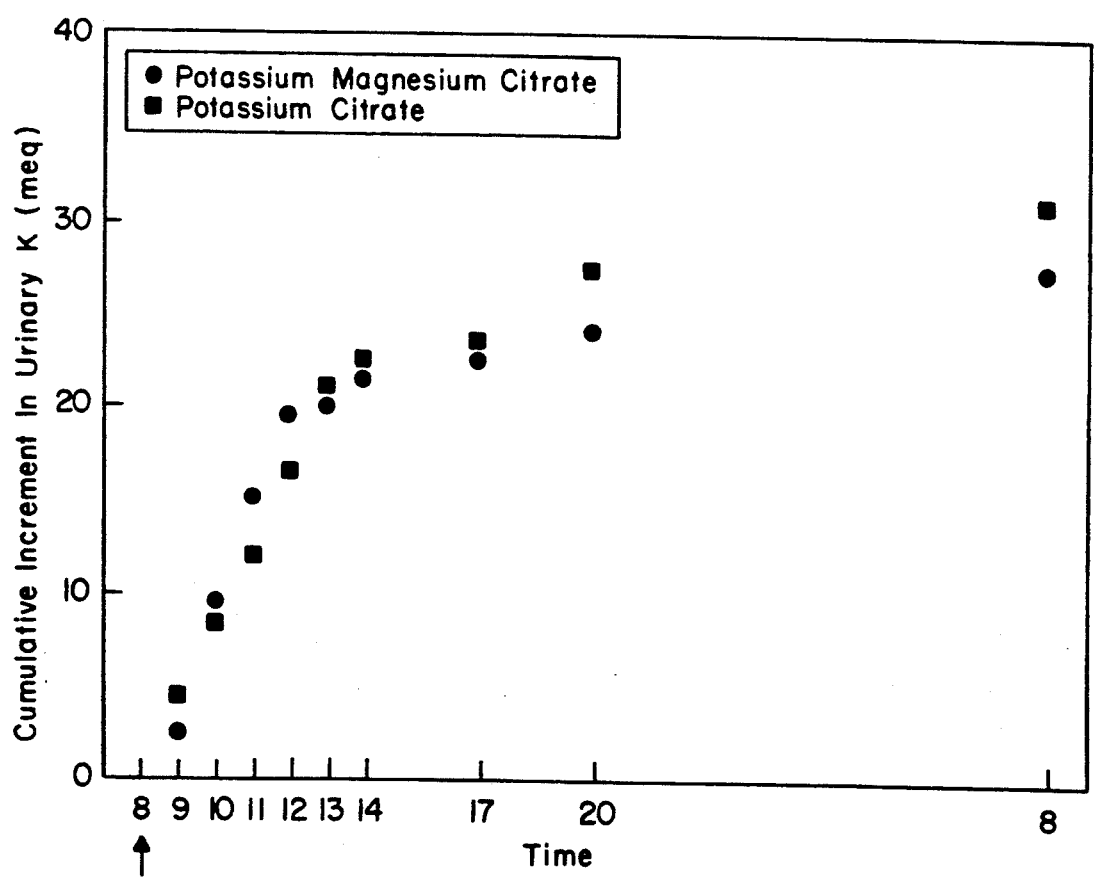
FIG. 2 is a graph demonstrating the comparative effects of potassium magnesium citrate and potassium citrate on urinary potassium.

Potassium bioavailability from potassium magnesium citrate was compared with that of potassium citrate. At each time period, the difference in urinary potassium following ingestion of potassium magnesium citrate (containing 49 meq potassium) or potassium citrate (containing 50 meq potassium) from that obtained at a corresponding time period following taking magnesium citrate (no potassium; therefore serving as control). The cumulative increment in urinary potassium (indicative of potassium bioavailability) is shown in FIG. 2. As shown, potassium bioavailability was equivalent between the two preparations (potassium magnesium citrate and potassium citrate).

Figure 3:
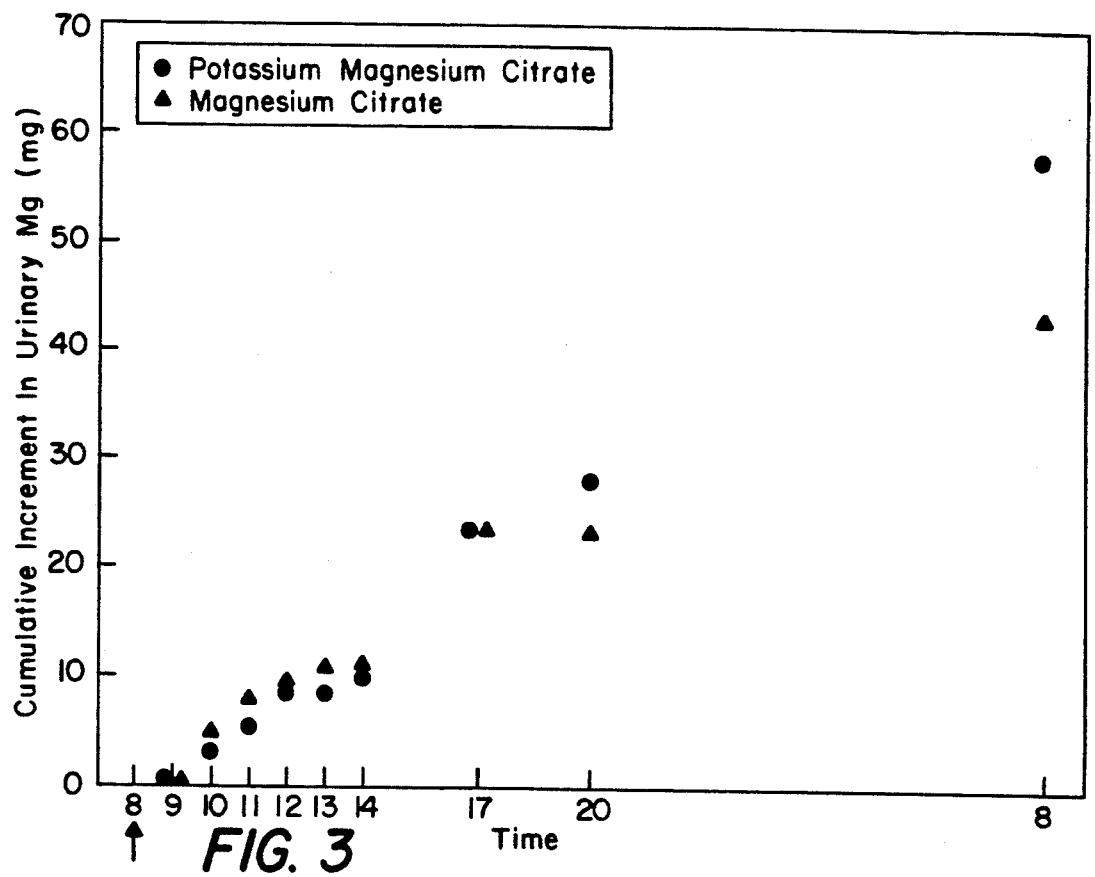
FIG. 3 is a graph demonstrating the comparative effects of potassium magnesium citrate and magnesium citrate on urinary magnesium.

Magnesium bioavailability from potassium magnesium citrate was compared with that of magnesium citrate. At each time period (following oral administration), the difference in urinary magnesium following ingestion of potassium magnesium citrate (containing 24.5 meq magnesium) or magnesium citrate (containing 25 meq magnesium) from that obtained at a corresponding time period following taking potassium citrate (no magnesium, thus serving as control) was calculated. The cumulative increment in urinary magnesium (indicative of magnesium bioavailability or absorption) is shown in FIG. 3. Note equivalent magnesium bioavailability between the two preparations.

Figure 4:
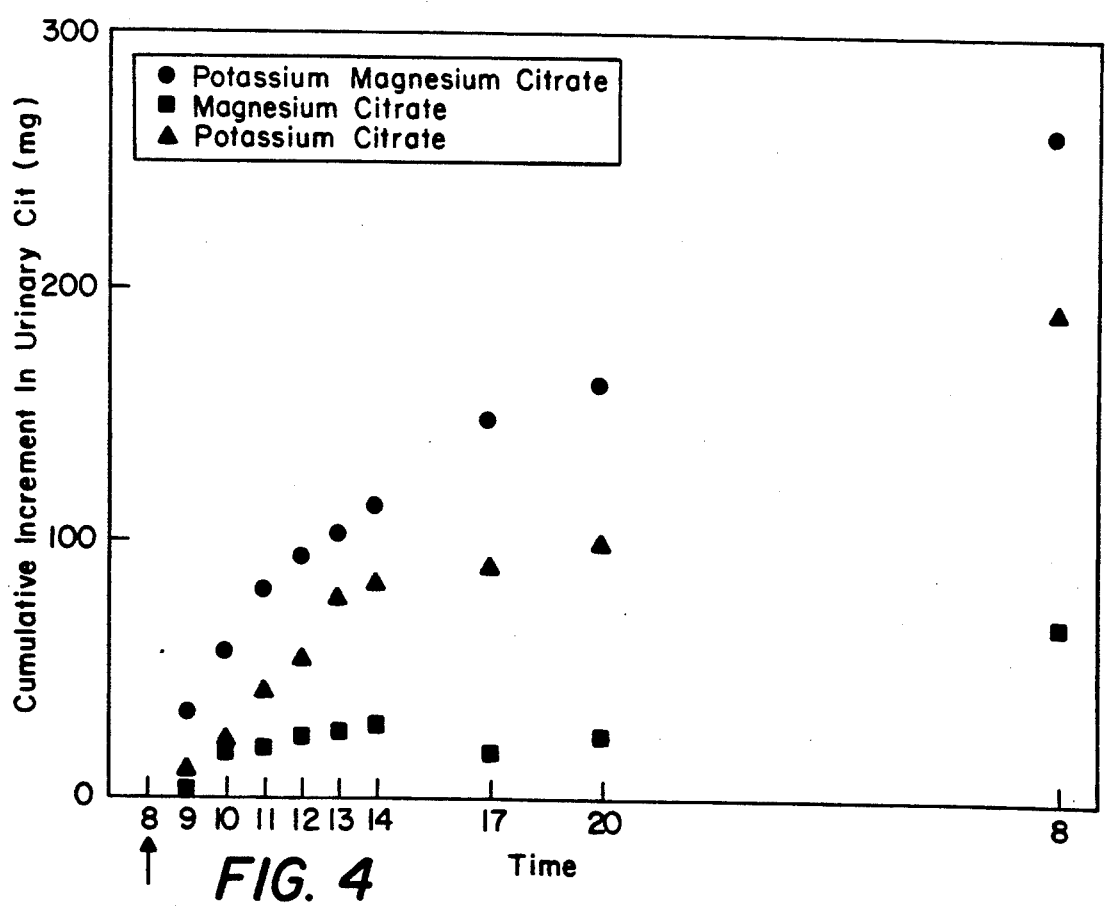
FIG. 4 is a graph demonstrating the comparative effects of potassium magnesium citrate, magnesium citrate and potassium citrate on urinary citrate.

Citrate bioavailability from potassium magnesium citrate was compared with that of potassium citrate and magnesium citrate. At each time period, the difference in urinary citrate following administration of potassium magnesium citrate (73.5 meq citrate), potassium citrate (50 meq citrate) or magnesium citrate (25 meq citrate) from that obtained following ingestion of potassium chloride (containing no citrate, thus serving as control) was calculated. The cumulative increment in citrate was much higher for potassium magnesium citrate than for the other two preparations, as shown in FIG. 4.

EXAMPLE 8

A study was done to demonstrate the comparative physiological-physiochemical action of tetrapotassium monomagnesium dicitrate prepared as disclosed herein when administered orally in accordance with the method of the invention. The study was performed with two patients, and the results are detailed below:

Each patient underwent five phases of study: placebo, potassium chloride, potassium citrate, magnesium citrate, and potassium-magnesium citrate. The results (mean values for the two patients) are outlined in Table 1. Compared to potassium chlorlde, potassium magnesium citrate gave a higher urinary pH, magnesium, and citrate. Compared to potassium citrate, potassium magnesium citrate produced a greater citrate excretion as magnesium citrate, potassium magnesium citrate gave higher values for urinary pH and citrate. Finally, compared to the placebo, potassium magnesium citrate produced higher values for urinary pH, magnesium, potassium and citrate, and lower values for urinary calcium and oxalate.

TABLE 1

| | Physiological Effects | | | | |
|---|---|---|---|---|---|
| | Placebo | Potassium Chloride | Potassium Citrate | Magnesium Citrate | Potassium-Mg Citrate |
| No tablets/d | 7 | 7 | 10 | 2.5 | 7 |
| K content, meq/d | 0 | 49 | 50 | 0 | 49 |
| Mg content, meq/d | 0 | 0 | 0 | 25 | 24.5 |
| Citrate content, meq/d | 0 | 0 | 50 | 25 | 73.5 |
| Urinary | | | | | |
| pH | 6.26 | 5.84 | 6.93 | 6.13 | 6.94 |
| Ca,mg/d | 145 | 103 | 86 | 137 | 106 |
| Mg,mg/d | 64 | 73 | 69 | 113 | 116 |
| Na,meq/d | 95 | 81 | 91 | 82 | 92 |
| K,meq/d | 31 | 90 | 80 | 38 | 73 |
| Citrate, mg/d | 498 | 636 | 821 | 718 | 968 |
| Oxalate, mg/d | 27 | 27 | 27 | 23 | 23 |

It is expected that potassium magnesium citrate should be equally effective as potassium chloride in preventing thiazide-induced hypokalemia, except in rare patients with severe chloride deficiency. Potassium magnesium citrate might be more effective than potassium citrate in augmenting citrate excretion, due to the "citraturic action" of magnesium, and the higher content of citrate. Moreover, the provision of magnesium as potassium magnesium citrate should augment urinary magnesium (from absorbed magnesium) and reduce urinary oxalate (from binding of oxalate by magnesium in the intestinal tract). Potassium magnesium citrate should also cause a greater enhancement of citrate excretion than magnesium citrate, because of its greater citrate content. Finally, it is theoretically possible that alkali load from potassium magnesium citrate might cause a further reduction in calcium excretion. This action might oppose the modest calciuric action of magnesium. Potasium magnesium citrate should therefore be more effective than potassium citrate or magnesium citrate in lowering urinary saturation of calcium oxalate and in increasing its inhibitor activity.

Thus, it is seen that the method of the present invention provides advantages and benefits not previously available in the production and use of dietary supplements comprising magnesium and potassium. Furthermore, it will be apparent to those skilled in the pharmaceutical arts upon reading this disclosure that other trace elements and minerals can also be compounded with the composition of the invention to produce other useful preparations. For this reason, it is intended that the invention disclosed herein be limited only by the broadest interpretation of the appended claims to which the inventors may be legally entitled.

We claim:

1. A method for supplementing dietary potassium and magnesium to overcome renal potassium and magnesium loss induced by thiazide therapy, comprising orally administering potassium magnesium citrate in a single salt consisting essentially of potassium, magnesium and citrate ions in a ratio of about 4:1:2 to a subject in need of such supplementation in the form of tablets each comprising up to about 7 meq potassium, 3.5 meq magnesium and 10.5 meq citrate.

2. The method of claim 1 wherein said salt is administered in tablets each comprising about 978 mg of potassium magnesium citrate.

3. The method of claim 1 wherein said salt is administered in tablets each having a density of about 1.6 g/cc.

* * * * *

UNITED STATES PATENT AND TRADEMARK OFFICE
CERTIFICATE OF CORRECTION

PATENT NO.   : 5,219,889
DATED        : June 15, 1993
INVENTOR(S)  : Neill B. Walsdorf et al It is certified that error appears in the above-identified patent and that said Letters Patent is hereby corrected as shown below:

Column 3, lines 9 and 10, change the equation to read:

$$4K^+ + Mg^{2+} + 2H_3C_6H_5O_7 \longrightarrow K_4Mg(C_6H_5O_7)_2 + 6H^+$$

Column 3, lines 19 and 20, change the equation to read:

$$K^+ + Mg^{2+} + H_3C_6H_5O_7 \longrightarrow KMgC_6H_5O_7 + 3H^+$$

Signed and Sealed this

Eighth Day of February, 1994

Attest:

BRUCE LEHMAN

Attesting Officer    Commissioner of Patents and Trademarks